(12) United States Patent
Chen

(10) Patent No.: US 10,799,195 B2
(45) Date of Patent: Oct. 13, 2020

(54) SYSTEM AND METHOD FOR POSITRON EMISSION TOMOGRAPHY

(71) Applicant: SHANGHAI UNITED IMAGING HEALTHCARE CO., LTD., Shanghai (CN)

(72) Inventor: Ze Chen, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 15/692,163

(22) Filed: Aug. 31, 2017

(65) Prior Publication Data

US 2019/0000403 A1    Jan. 3, 2019

Related U.S. Application Data

(63) Continuation of application No. PCT/CN2017/091093, filed on Jun. 30, 2017.

(51) Int. Cl.
*A61B 6/03* (2006.01)
*A61B 6/00* (2006.01)
*G01T 1/29* (2006.01)

(52) U.S. Cl.
CPC ............ *A61B 6/037* (2013.01); *A61B 6/4208* (2013.01); *G01T 1/2985* (2013.01); *A61B 6/4266* (2013.01);
(Continued)

(58) Field of Classification Search
None
See application file for complete search history.

(56) References Cited

U.S. PATENT DOCUMENTS

| 4,823,016 A | 4/1989 | Yamashita et al. |
| 7,385,201 B1 * | 6/2008 | Joung ............... G01T 1/2018 250/370.01 |

(Continued)

FOREIGN PATENT DOCUMENTS

| CN | 201555955 U | 8/2010 |
| CN | 101937095 A | 1/2011 |

(Continued)

OTHER PUBLICATIONS

International Search Report in PCT/CN2017/091093 dated Apr. 3, 2018, 5 pages.

(Continued)

*Primary Examiner* — Edwin C Gunberg
(74) *Attorney, Agent, or Firm* — Metis IP LLC

(57) ABSTRACT

A method and system for using in a Positron Emission Tomography (PET) system. The PET system comprises at least one processor and a storage. The PET system comprises an acquisition module and a processing module. The acquisition module is configured to acquire a PET data set corresponding to a target object. The acquisition module comprises a first light sensor array, a second light sensor array, and a scintillator array. The processing module is configured to determine a three-dimensional position of an incidence photon based on the PET data set. The first number of light sensors in the first light sensor array and the second number of light sensors of the second light sensor array is less than the number of scintillator of the scintillator array.

20 Claims, 13 Drawing Sheets

(52) U.S. Cl.
CPC ........... *A61B 6/4275* (2013.01); *A61B 6/4417* (2013.01); *A61B 6/5205* (2013.01)

(56) References Cited

U.S. PATENT DOCUMENTS

| | | | |
|---|---|---|---|
| 8,880,144 B2* | 11/2014 | Kang | G01T 1/2935 |
| | | | 250/363.03 |
| 9,207,334 B1 | 12/2015 | Ito et al. | |
| 9,575,192 B1 | 2/2017 | Ng et al. | |
| 9,599,731 B2 | 3/2017 | Schulz et al. | |
| 2005/0072904 A1 | 4/2005 | Aykac et al. | |
| 2005/0253073 A1 | 11/2005 | Joram et al. | |
| 2006/0197025 A1 | 9/2006 | Burr et al. | |
| 2009/0134334 A1* | 5/2009 | Nelson | G01T 1/2002 |
| | | | 250/361 R |
| 2010/0074396 A1* | 3/2010 | Schmand | A61B 6/032 |
| | | | 378/19 |
| 2010/0176301 A1 | 7/2010 | Wieczorek et al. | |
| 2011/0121192 A1 | 5/2011 | Moriya et al. | |
| 2011/0155898 A1 | 6/2011 | Burr et al. | |
| 2011/0263965 A1 | 10/2011 | Kang et al. | |
| 2013/0056638 A1 | 3/2013 | Inadama et al. | |
| 2014/0264041 A1 | 9/2014 | Schulz et al. | |
| 2014/0301534 A1 | 10/2014 | Rao et al. | |
| 2015/0028218 A1 | 1/2015 | Kataoka et al. | |
| 2015/0378034 A1 | 12/2015 | Dowaki et al. | |
| 2016/0070006 A1 | 3/2016 | Konkle et al. | |
| 2016/0084703 A1 | 3/2016 | Shaber | |
| 2016/0170045 A1 | 6/2016 | Kim | |
| 2016/0242706 A1 | 8/2016 | Tsuda et al. | |
| 2017/0371043 A1 | 12/2017 | Schulz | |
| 2018/0059266 A1 | 3/2018 | Berker et al. | |

FOREIGN PATENT DOCUMENTS

| | | |
|---|---|---|
| CN | 102451017 A | 5/2012 |
| CN | 102565840 A | 7/2012 |
| CN | 104570042 A | 4/2015 |
| CN | 107495980 A | 12/2017 |
| CN | 107684436 A | 2/2018 |
| JP | 2010101682 A | 5/2010 |

OTHER PUBLICATIONS

Written Opinion in PCT/CN2017/091093 dated Apr. 3, 2018, 4 pages.

* cited by examiner

710

_US 10,799,195 B2_

SYSTEM AND METHOD FOR POSITRON EMISSION TOMOGRAPHY

CROSS-REFERENCE TO RELATED APPLICATIONS

This present application is a continuation of International Application No. PCT/CN2017/091093, filed on Jun. 30, 2017, designating the United States of America, the contents of which are hereby incorporated by reference.

TECHNICAL FIELD

The present disclosure generally relates to a medical system, and more specifically relates to methods and systems for determining a three-dimensional position of an incidence photon in a positron emission tomography (PET), and/or single photon emission computed tomography (SPECT).

BACKGROUND

PET and SPECT imaging devices operate by sensing incidence photons (e.g., gamma photons) emitted by radiopharmaceuticals that have been accumulated in target organs or tissues of a patient. A two-dimensional or three-dimensional image is constructed based on positions of particular annihilation events. The positions of particular annihilation events may be determined based on positions of incidence photons corresponding to the particular annihilation events. There is a need for a system and a method for determining the positions of incidence photons more accurately.

SUMMARY

The present disclosure relates to a Positron Emission Tomography (PET) system. One aspect of the present disclosure relates to the PET system comprising at least one processor and a storage. The PET system may comprise an acquisition module and a processing module. The acquisition module may comprise a first light sensor array, a second light sensor array, and a scintillator array. The acquisition module may be configured to acquire a PET data set corresponding to a target object. The first light sensor array may be optically coupled to a first surface of the scintillator array. The second light sensor array may be optically coupled to a second surface of the scintillator array. A first number of the light sensors in the first light sensor array may be less than a number of scintillator elements in the scintillator array. A second number of the second light sensor array may be less than a number of scintillator elements in the scintillator array.

In some embodiments, the PET system may further comprise a processing module. The processing module may be configured to determine the three-dimensional position of the incidence photon based on the PET data set.

In some embodiments, at least one light sensor in the first light sensor array or the second light sensor array may comprise a silicon photomultiplier (SiPM).

In some embodiments, an image reconstruction unit may be configured to reconstruct an image of the target object based on the three-dimensional position of the incidence photon and the PET data set.

In some embodiments, at least one component of the three-dimensional position of the incidence photon in a direction may be determined based on a light intensity spatial distribution corresponding to the incidence photon in the direction.

In some embodiments, the PET data set may comprise a first data set comprising at least a first light intensity value corresponding to the incidence photon detected by the first light sensor array, and a second data set may comprise at least a second light intensity value corresponding to the incidence photon detected by the second sensor array.

In some embodiments, a first dimensional position of the incidence photon in a first direction may be determined based on the first data set. A second dimensional position of the incidence photon in a second direction may be determined based on the second data set. A third dimensional position of the incidence photon in a third direction may be determined based on the first data set and the second data set.

In some embodiments, at least one component of the three-dimensional position of the incidence photon in a direction may be related to a coefficient. The coefficient may be a ratio of a sum of the at least first light intensity value in the first data set and a sum of the at least second light intensity value in the second data set.

In some embodiments, the ratio of the first number of light sensors of the first light sensor array to the number of the plurality of scintillators may be 2 to 1. The ratio of the second number of light sensors of the second light sensor array to the number of the plurality of scintillators may be 2 to 1.

In some embodiments, the first number of light sensors of the first light sensor array is equal to the second number of light sensors of the second light sensor array.

Another aspect of the present disclosure relates to a method for determining a three-dimensional position of an incidence photon in a Positron Emission Tomography (PET) system. The method may be implemented on at least one processor and a storage. The method may include one or more of the following operations. A PET data set corresponding to a target object may be acquired by the PET system. The three-dimensional position of the incidence photon may be determined based on the PET data set.

A further aspect of the present disclosure relates to a non-transitory computer readable medium including executable instructions. The instructions, when executed by at least one processor, may cause the at least one processor to effectuate a method for determining a three-dimensional position of an incidence photon using in a Positron Emission Tomography (PET) system. In some embodiments, the non-transitory computer readable medium may include instructions for causing a computer to implement the method described herein.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1A:
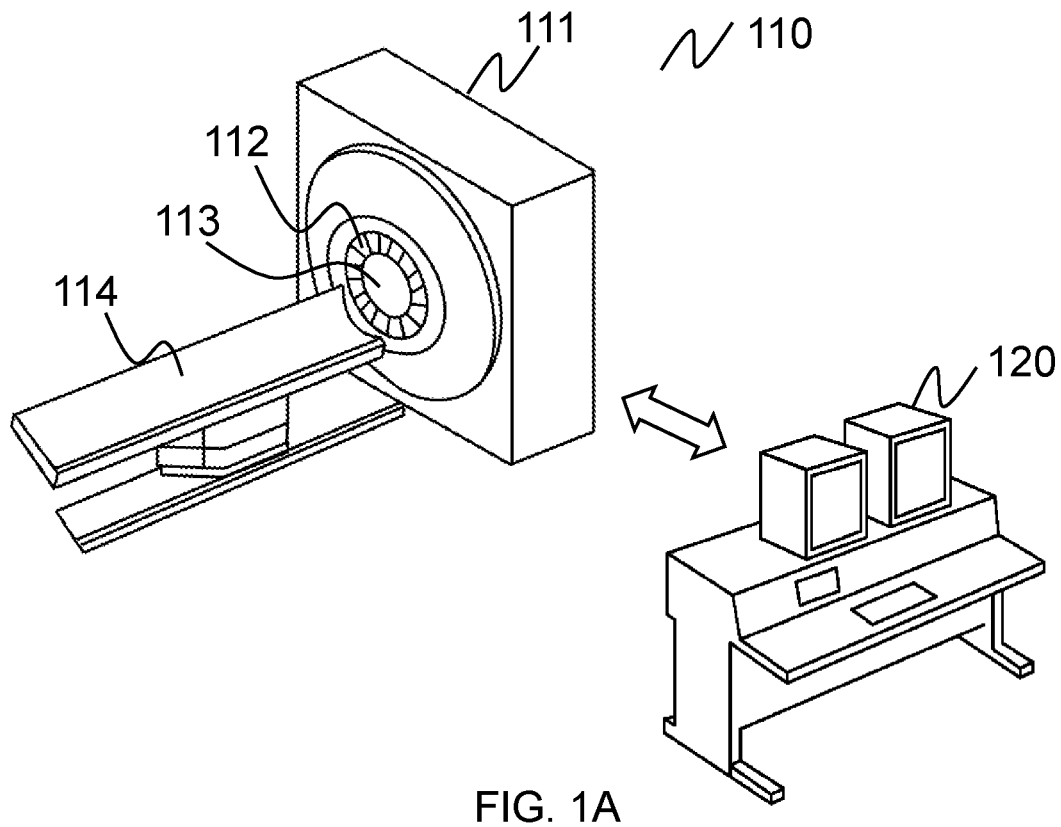
FIG. 1A is a schematic diagram illustrating an exemplary Positron Emission Tomography (PET) system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by other expression if they achieve the same purpose.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnostic or research purposes. The imaging system may find its applications in different fields such as medicine or industry. For example, the imaging system may be used in internal inspection of components including, for example, flaw detection, security scanning, failure analysis, metrology, assembly analysis, void analysis, wall thickness analysis, or the like, or any combination thereof.

For illustration purposes, the disclosure describes systems and methods for determining a three-dimensional position of an incidence photon in a PET system. The PET system may determine the three-dimensional position of an incidence photon based on a PET data set. As used herein, a PET data set may refer to a plurality of sub data sets acquired by the PET system. For example, the PET data may include a first data set corresponding to a first direction and a second data set corresponding to a second direction in a three-dimensional coordinate system. The three-dimensional position of the incidence photon may be determined based on the first data set and the second data set.

The following description is provided to help better understanding methods or systems for determining a three-dimensional position of an incidence photon. The term "incidence photon" used in this disclosure may refer to gamma (γ) rays, X rays, etc. The term "three-dimensional position" used in this disclosure may refer to a position represented in three different directions (e.g., in a three-dimensional system). The determination process may be executed by a PET system, a SPECT system, or other imaging system. The determination result may be used for subsequent image reconstruction in the imaging system. This is not intended to limit the scope the present disclosure. For persons having ordinary skills in the art, a certain amount of variations, changes, and/or modifications may be deducted under guidance of the present disclosure. Those variations, changes, and/or modifications do not depart from the scope of the present disclosure.

FIG. 1A is a schematic diagram illustrating an exemplary Positron Emission Tomography (PET) system according to some embodiments of the present disclosure. In some embodiments, the PET system may be a multi-modality system. The exemplary multi-modality system may include a computed tomography-positron emission tomography (CT-PET) system, a magnetic resonance-positron emission tomography (MR-PET) system, etc. In some embodiments, the multi-modality imaging system may include modules and/or components for performing PET imaging and/or related analysis.

The PET system may include a PET scanner 110 and a host computer 120. The PET scanner 110 may include a gantry 111, a detector 112, a detecting region 113, and a subject table 114.

The detector 112 may detect radiation events (e.g., gamma photons) emitted from the detecting region 113. In some embodiments, the detector 112 may include a plurality of detector units (e.g., a detector unit 310 shown in FIG. 3, a detector unit 315 shown in FIG. 3). The detector units may be implemented in any suitable manner, for example, in a ring-shape detector, in a rectangle-shape detector, or in an array implemented on any shaped detector. In some embodiments, the plurality of detector units may be implemented on the detector 112 symmetrically, such as the detector unit 310 and 315 shown in FIG. 3. In some embodiments, the detector unit may include one or more crystal elements and/or one or more photomultiplier tubes (PMT) (not shown). In some embodiments, a PMT as employed in the present disclosure may be a single-channel PMT or a multi-channel PMT. The subject table 114 may position a subject in the detecting region 113.

In some embodiments, the detected radiation events may be stored or archived in a storage (e.g., a storage device in the host computer 120), displayed on a display (e.g., a display of or attached to the host computer 120), or transferred to an external storage device (e.g., an external storage device attached to the host computer 120 via a cable, or a wired or wireless network). In some embodiments, a user may control the PET scanner 110 via the host computer 120.

Further, while not shown, the PET system may be connected to a network (e.g., a telecommunications network, a local area network (LAN), a wireless network, a wide area network (WAN) such as the Internet, a peer-to-peer network, a cable network, etc.) for communication purposes.

It should be noted that the above description of the PET system is merely provided for the purposes of illustration, and not intended to limit the scope of the present disclosure. For persons having ordinary skills in the art, multiple variations and modifications may be made under the teachings of the present disclosure. For example, the assembly and/or function of the PET system may be varied or changed according to specific implementation scenarios. Merely by way of example, some other components may be added into the PET system, such as a patient positioning module, a gradient amplifier module, and other devices or modules. As another example, the storage module 133 may be optional, and the modules in the PET system may include an integrated storage unit respectively.

Figure 1B:
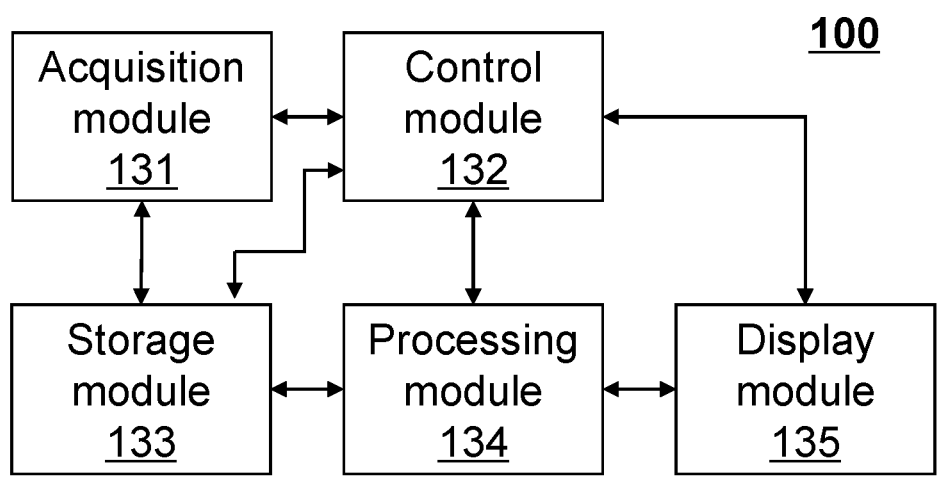
FIG. 1B is a block diagram illustrating an exemplary image processing system according to some embodiments of the present disclosure.

FIG. 1B is a block diagram illustrating an exemplary image processing system 100 according to some embodiments of the present disclosure. The image processing system 100 may be implemented via the host computer 120. As illustrated in FIG. 1B, the image processing system 100 may include an acquisition module 131, a control module 132, a storage module 133, a processing module 134, and a display module 135.

The acquisition module 131 may acquire or receive a PET data set. Merely by way of example, the PET data set may include one or more sub data set (e.g., a first data set described below in connection with in FIG. 7C and a second data set described below in connection with in FIG. 7D). In some embodiments, during a PET scan or analysis, a PET tracer may be first introduced into the subject before a scanning process begins. During the PET scan, the PET tracer may emit positrons, namely the antiparticles of electrons. A positron has the same mass and the opposite electrical charge as an electron, and it undergoes an annihilation (also referred to as an "annihilation event" or a "coincidence event") with an electron (that may naturally exist in abundance within the subject) as the two particles collide. An electron-positron annihilation event (e.g., a positron-electron annihilation event 340 described below in connection with in FIG. 3) may result in two 511 keV gamma photons. Upon the generation of the two gamma photons in response to the electron-positron annihilation event, the two gamma photons begin to travel in opposite directions with respect to one another. The line connecting the two gamma photons may be referred to as a "line of response (LOR)." The acquisition module 131 may obtain the trajectory and/or information of the gamma photons (also referred to as the "PET data set"). For example, the PET data set may include data acquired from the detectors 112 corresponding to the two gamma photons. In some embodiments, the PET data set may be used to determine three-dimensional positions of the two gamma photons.

In some embodiments, the PET tracer may include carbon (11C), nitrogen (13N), oxygen (15O), fluorine (18F), or the like, or a combination thereof. Accordingly, in some embodiments, the PET tracer of the present disclosure may be organic compounds containing one or more of such isotopes. These tracers are either similar to naturally occurred substances or otherwise capable of interacting with the functionality or activity of interest within the subject.

The control module 132 may generate one or more control parameters for controlling the acquisition module 131, the storage module 133, the processing module 134, and/or the display module 135. For example, the control module 132 may control the acquisition module 131 to determine as to whether to acquire a signal, or the time when a signal may be acquired. As another example, the control module 132 may control the processing module 134 to select different algorithms to process the PET data set acquired by the acquisition module 131. In some embodiments, the control module 132 may receive a real-time command provided by a user (e.g., a doctor) or a predetermined command retrieved by a user (e.g., a doctor) from a storage device. The control module 132 may further apply the real-time command or the predetermined command to adjust the acquisition module 131, and/or the processing module 134 to take images of a subject according to the received command. In some embodiments, the control module 132 may communicate with other modules in the image processing system 100 for exchanging information or data.

The storage module 133 may store the acquired PET data set, the control parameters, the processed PET data set, or the like, or a combination thereof. In some embodiments, the storage module 133 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage module 133 may store one or more programs and/or instructions that may be executed by one or more processors of the image processing system 100 (e.g., the processing module 134) to perform exemplary methods described in this disclosure. For example, the storage module 133 may store program(s) and/or instruction(s) executed by the processor(s) of the image processing system 100 to acquire a PET data set, determine a position of an incidence photon, or display any intermediate result or a resultant position.

The processing module 134 may process information received from modules in the image processing system 100. In some embodiments, the processing module 134 may pre-process the PET data set acquired by the acquisition module 131, or retrieved from the storage module 133. In some embodiments, the processing module 134 may determine three-dimensional positions of incidence photons based on the processed PET data set, reconstruct an image based on the determined positions of incidence photons and the PET data set, generate reports including one or more PET images and/or other related information, or the like. For example, the processing module 134 may process the PET data set based on a pre-processing operation including data classification, data screening, data correction (e.g., correction for random coincidences, detector dead-time correction, detector-sensitivity correction), data estimation and subtraction (estimation and subtraction of scattered photons), or the like, or any combination thereof. As another example, the processing module 134 may determine a plurality of pairs of a first data set and a second data set based on the PET data set corresponding to a plurality of incidence protons (e.g., gamma protons).

The display module 135 may display any information relating to the image processing system 100. The information may include programs, software, algorithms, data, text, number, images, voice, or the like, or any combination thereof. In some embodiments, the display module 135 may include a liquid crystal display (LCD), a light emitting diode (LED) based display, a flat panel display, a cathode ray tube (CRT), a touch screen, or the like, or a combination thereof. The touch screen may include, for example, a resistance touch screen, a capacity touch screen, a plasma touch screen, a vector pressure sensing touch screen, an infrared touch screen, or the like, or a combination thereof.

In some embodiments, one or more modules illustrated in FIG. 1B may be implemented in at least part of the exemplary ECT system illustrated in FIG. 1A. For example, the acquisition module 131, the control module 132, the storage module 133, the processing module 134, and/or the display module 135 may be integrated into a console. Via the console, a user may set parameters for scanning, control the imaging procedure, control a parameter of the reconstruction of an image, view the reconstructed images, etc. In some embodiments, the console may be implemented via the host computer 120.

Figure 2:
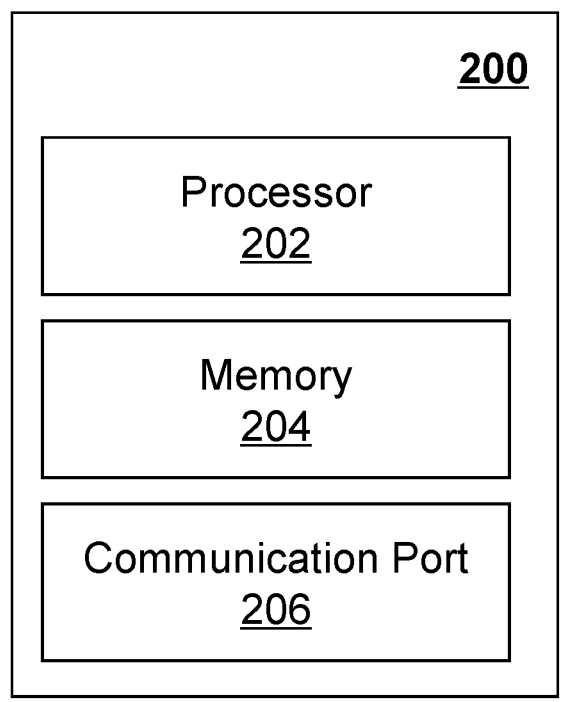
FIG. 2 is a block diagram illustrating exemplary hardware and software components of a computing device according to some embodiments of the present disclosure.

FIG. 2 is a block diagram illustrating exemplary hardware and software components of a computing device 200 on which the image processing system 100 may be implemented according to some embodiments of the present disclosure. In some embodiments, the computing device 200 may include a processor 202, a memory 204, and a communication port 206.

The processor 202 may execute computer instructions (program code) and perform functions of the processing module 134 in accordance with techniques described herein. Computer instructions may include routines, programs, objects, components, data structures, procedures, modules, and functions, which perform particular functions described herein. For example, the processor 202 may process the data or information received from the acquisition module 131, the control module 132, the storage module 133, or any other component of the imaging system 100. In some embodiments, the processor 202 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof. For example, the processor 202 may include a microcontroller to process the PET data set from the PET scanner 110 for determining three-dimensional position of an incidence photon.

The memory 204 may store the data or information received from the acquisition module 131, the control module 132, the storage module 133, the processing module 134, or any other component of the imaging system 100. In some embodiments, the memory 204 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the memory 204 may store one or more programs and/or instructions to perform exemplary methods described in the present disclosure. For example, the memory 204 may store a program for the processing module 134 for determining a three-dimensional position of an incidence photon based on the ECT data set.

The communication port 206 may transmit to and receive information or data from the acquisition module 131, the control module 132, the storage module 133, the processing module 134 via network. In some embodiments, the communication port 206 may include a wired port (e.g., a Universal Serial Bus (USB) port, a High Definition Multimedia Interface (HDMI) port, or the like) or a wireless port (a Bluetooth port, an infrared interface, a WiFi port, or the like).

Figure 3:
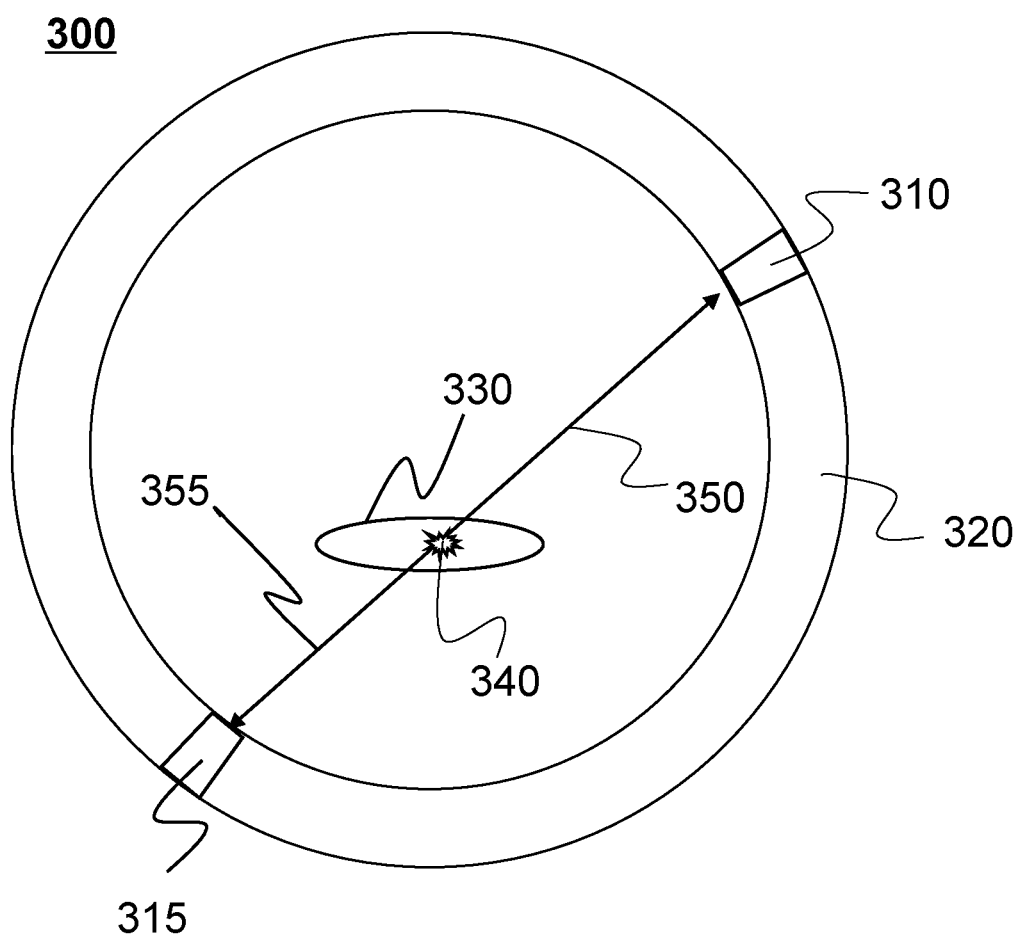
FIG. 3 illustrates a schematic diagram of an exemplary PET scanner according to some embodiments of the present disclosure.

FIG. 3 illustrates a schematic diagram of an exemplary PET scanner 300 according to some embodiments of the present disclosure. The PET scanner 300 may be an embodiment of the PET scanner 110 shown in FIG. 1A. The PET scanner 300 may include a detector ring 320 and a table 330, or the like.

The detector ring 320 may acquire a PET data set corresponding to a target object (not shown in FIG. 3). The detector ring 320 may include a plurality of detector units (e.g., a detector unit 310, a detector unit 315, etc.). The detector unit 310 and the detector unit 315 may be same or different type of detector. For example, the detector unit 310 and the detector 315 may both be block detector. The detector unit 310 and the detector unit 315 may include a plurality of light sensor elements (e.g., $Sx_1$ shown in FIG. 7B). The detector unit 310 may detect an incidence photon. The detector unit 310 may be an incidence photon detector, such as a gamma (γ) ray detector. The detector 310 may generate detected data (e.g., a first data set detected by a first light sensor array 410 shown in FIG. 4, a second data set detected by a second light sensor array 420 shown in FIG. 4) corresponding to the incidence photon. The detected data may be used to determine a three-dimensional position of the incidence photon.

The table 330 may be used to place a target object (not shown in FIG. 3) for scanning. The target object may be people, an animal, or other species.

In a PET scanning process, a radiopharmaceutical may be administered to the target object, in which the radioactive decay events of the radiopharmaceutical can produce positrons. A positron may interact with an electron to produce a positron-electron annihilation event 340 that emits two oppositely directed γ rays 350 and 355 in the opposite directions (as shown in FIG. 3). Using coincidence detection circuitry (not shown in FIG. 3), the detector ring 320 may detect the coincident events corresponding to the positron-electron annihilation event 340. For example, when two γ photons are determined to have been originated from the same positron-electron annihilation event 340, a coincident event is detected and a line of response (LOR) is drawn between the two points on the respective detectors where the two γ photons were detected. Further, a two- or three-dimensional image may be reconstructed based on the lines of response. For example, the PET scanner 300 may include multiple detector rings 320 and may allow the coincidence events to be detected between any two of the multiple detector rings 320 as well as within a single detector ring 320. When treating each of the multiple detector rings 320 as a single entity, a two-dimensional image may be reconstructed individually based on the lines of response detected by each of the multiple detector rings 320. When treating the multiple detector rings 320 as a single entity, three-dimensional images may be reconstructed based on all of the lines of response detected on the multiple detector rings 320. Therefore, distributions of the radiopharmaceutical in the target object may be determined based on the two- and/or three-dimensional images.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the PET scanner 300 may include a gantry to install the detector ring 320.

Figure 4:
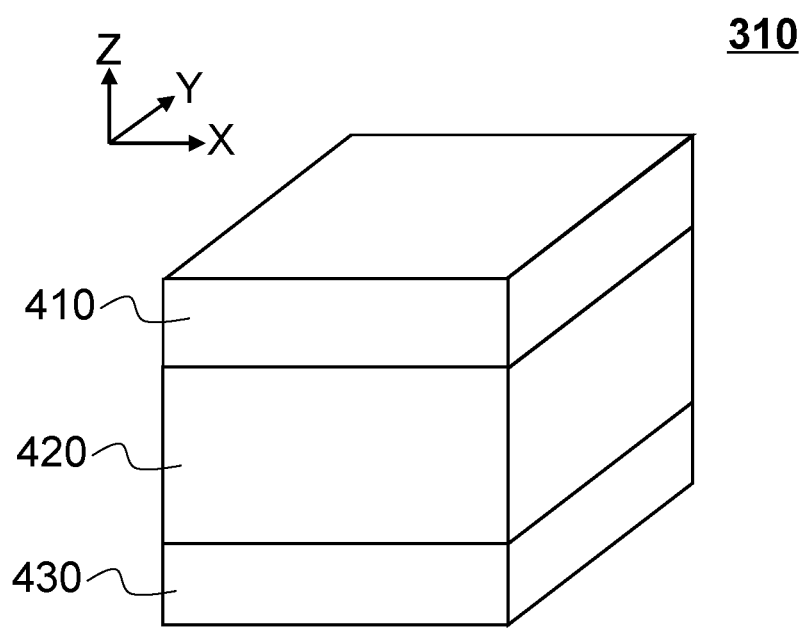
FIG. 4 illustrates a schematic diagram of an exemplary detector unit according to some embodiments of the present disclosure.

FIG. 4 illustrates a schematic diagram of an exemplary detector unit 310 according to some embodiments of the present disclosure. The detector unit 310 may include a multi-layer structure (e.g., a three-layer structure). The detector unit 310 may include a layer of a first light sensor array 410, a layer of a scintillator array 420, and a layer of a second light sensor array 430. In some embodiments, the first light array 410 may be attached to an upper plane of the scintillator array 420. The second light array 420 may be attached to a lower plane of the scintillator array 420. A three-dimensional coordinate system corresponding to the detector unit 310 may be determined (as shown in FIG. 4). Directions of X-axis, Y-axis, and Z-axis may be designated as a first direction, a second direction and a third direction. The X-Y plane of the three-dimensional coordinate system may be parallel to the upper plane and lower plane of the scintillator array 420. The X-Z plane of the three-dimensional coordinate system may be perpendicular to the upper plane and lower plane of the scintillator array 420.

The first light sensor array 410 and/or the second light sensor array 430 may be optically coupled with the scintillator array 420. The scintillator array 420 may generate light when struck by an incidence photon (e.g., a γ photon). The first light sensor array 410 and the second light sensor array 430 may detect the light.

The first light sensor array 410 may generate one or more electrical signals (e.g., voltage signals, current signals, etc.) based on the detecting of the light generated in responsive to the incidence photon. The first light sensor array 410 may determine a first data set based on the one or more electrical signals. Base on the first data set, a light intensity spatial distribution corresponding to the incidence photon in the first direction (e.g., X-axis in the three-dimensional coordinate system) may be determined.

In some embodiments, the first light sensor array 410 may include a plurality of light sensor elements (e.g., $Sx_1$, $Sx_2$, $Sx_3$, . . . , $Sx_i$, . . . ). The plurality of light sensors may be arranged in one or more rows (e.g., row 1, row 2 . . . row M shown in FIG. 6A). Each of the plurality of light sensors in the first light sensor array 410 may detect the light and generate an electrical signal. A light sensor in a row may connect through an electric circuit to another light sensor (e.g., an adjacent light sensor) in the same row and share a same electrical signal collection unit (not shown in FIG. 4). The plurality of light sensors may not connect to another light sensor in a same row and each of the plurality of light sensors may have an electrical signal collection unit (not shown in FIG. 4). With one or more operations, the plurality of light sensors may determine a first data set (e.g., $\{X_1, X_2, X_3, \ldots, X_i, \ldots\}$) based on the plurality of electrical signals at a time. The one or more operations may include performing an analog-to-digital conversion. A datum in the first data set may be acquired by a sensor in the light sensor array 410. For example, $X_1$ may be acquired by sensor $Sx_1$ at a time.

The second light sensor array 430 may generate one or more electrical signals (e.g., voltage signals, current signals, etc.) based on the detecting of the light corresponding to the incidence photon. The second light sensor 430 may determine a second data set based on the one or more electricals signals. Based on the second data set, a light intensity spatial distribution corresponding to the incidence photon in the second direction (e.g., Y-axis in the three-dimensional coordinate system) may be determined.

In some embodiments, the second light sensor array 430 may include a plurality of light sensor elements (e.g., $Sy_1$, $Sy_2$, $Sy_3$, ..., $Sy_i$, ...). The plurality of light sensors may be arranged in one or more columns (e.g., column 1, column 2 ... column N shown in FIG. 6B). Each of the plurality of light sensors in the second sensor array 430 may detect the light and generate an electrical signal. A light sensor in a column may connect through an electric circuit to another light sensor (e.g., an adjacent light sensor) in the same column and share a same electrical signal collection unit (not shown in FIG. 4). The plurality of light sensors may not connect to another light sensor in a same column and each of the plurality of light sensors may have an electrical signal collection unit (not shown in FIG. 4). With one or more operations, the plurality of light sensors may determine a second data set (e.g., $\{Y_1, Y_2, Y_3, \ldots, Y_i, \ldots\}$) based on the plurality of electrical signals at a time. The one or more operations may include performing an analog-to-digital conversion. A datum in the second data set may be acquired by a sensor in the second light sensor array 430. For example, $Y_1$ may be acquired by sensor $Sy_1$.

Light sensors in the first light sensor array 410 and the second light sensor array 430 may be same or different type of detector. The light sensors may include silicon photomultipliers (SiPMs), avalanched photodiodes (APDs), photomultiplier tubes (PMTs), etc. The light sensors in the first light sensor array 410 and the second light sensor array 430 may be arranged uniformly or ununiformly in their separation distance, sensor number density, or the like. For example, a separation distance of each two adjacent light sensors in the first light sensor 410 and the second light sensor array 430 may be same. As another example, a number of light sensors in each of the first light sensor array 410 and the second light sensor array 430 in the first direction (e.g., X-axis in the three-dimensional coordinate system) and the second direction (e.g., Y-axis in the three-dimensional coordinate system) may be same. A number of the light sensors in the first light sensor array 410 and a number of the light sensors in the second light sensor array 430 may be the same or different.

The scintillator array 420 may include one or more scintillators (i.e., scintillator elements). The scintillators may be arranged in one or more rows (e.g., K rows shown in FIG. 5A) and one or more columns (e.g., P columns shown in FIG. 5B). The scintillators may further be arranged in one or more layers. The scintillators may be used to record ionizing radiation (e.g., γ rays). In the PET scanner 300, the radiation may be generated by the annihilation of positrons emitted by an administered radiopharmaceutical. For example, when a scintillator receives a γ photon, the γ photon may travel a certain distance within the scintillator before it is finally absorbed by the scintillator. The distance is known as the depth of interaction (DOI). At the position where the γ photon is absorbed, the scintillator may convert a fraction of the absorbed energy into visible or ultraviolet photons. The conversion process may produce a pulse of light corresponding to each γ photon that interacts with the scintillator. An intensity of the pulse of light is usually proportional to the energy deposited in the scintillator.

The scintillators in the scintillator array 420 may be any type of scintillator with one or more physical properties and/or scintillation properties (e.g., intensity, effective atomic number, decay time, light output, emission wave length, energy resolution, transparent at emission wavelength, index of refraction, radiation hard, nonhygroscopic, rugged, and economic growth process, etc.). For example, the intensity of the scintillator in the scintillator array 420 may be from 3.00 $g/cm^3$ to 10 $g/cm^3$. For another example, the effective atomic number of the scintillator in the scintillator array 420 may be from 10 to 100. As another example, the emission wave length of the emission wave length may be near 400 nm. Exemplary materials suitable for the scintillators in the scintillator array 410 may include sodium iodide (NaI), cesium iodide (CsI), lanthanum bromide ($LaBr_3$), lanthanum chloride ($LaCl_3$), lutetium oxyorthosilicate ($Lu_2SiO_5$), lutetium yttrium orthosilicate (LYSO), lutetium pyrosilicate, bismuth germinate (BGO), gadolinium orthosilicate (GSO), lutetium gadolinium orthosilicate, barium fluoride ($BaF_2$), yttrium aluminate ($YAlO_3$), or the like, or any combination thereof.

The scintillators in the scintillator array 410 may be in multiple shapes. For example, the scintillators may be in a shape of sphere, cuboid, rod, wire, ramp, columns or disks with various cross-sectional shapes, or the like, or a combination thereof. The scintillators may be liquid or solid, organic or inorganic, and crystalline or non-crystalline. Herein taking a crystalline structure as an example, the crystalline structure may include a single-layer crystal and a multilayer crystal. The single-layer crystal may include only one layer of crystal. The multilayer crystal may comprise more than one layer of crystal. The scintillators in the scintillator array 410 may be in different sizes. Different sizes of the scintillator may correspond to different energy resolution levels. There may be a particular size in which the scintillators demonstrate an optimal energy resolution. The scintillators in the scintillator array 410 may be arranged uniformly or ununiformly in their separation distance, scintillator number density, or the like. For example, a separation distance of each two adjacent scintillators may be same. As another example, scintillator number density in a first area of the scintillator array 410 (e.g., an area from column 1 to column 3) and scintillator number density of a second area of the scintillator array 410 (e.g., an area from column 11 to column 13) may be different.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the detector unit 310 may include one or more light guides and/or collimators between the first light sensor array 410 and the scintillator array 420 for guiding the light emitted from the scintillator array 420 to the first light sensor array 410.

Figure 5A:
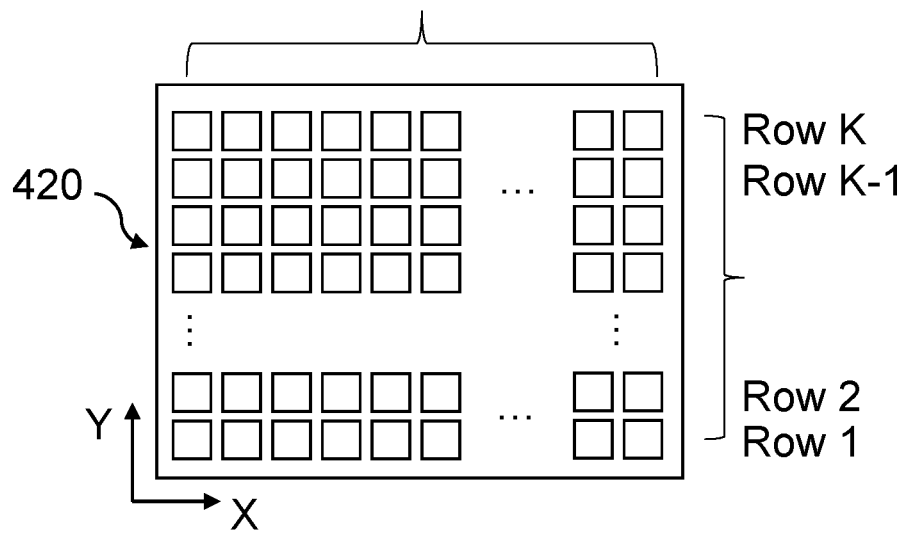
FIG. 5A illustrates a top view of an exemplary scintillator array according to some embodiments of the present disclosure.

FIG. 5A illustrates a top view of an exemplary scintillator array 420 according to some embodiments of the present disclosure. The top view is a view of the X-Y plane of the scintillator array 420. As shown in FIG. 5A, the scintillator array 420 may include a plurality of scintillators.

The scintillator array 420 may be a single-layer array or a multi-layer array. When the scintillator array 420 is a single-layer array with K rows and P columns, a number of scintillator elements (e.g., scintillators) in the scintillator array 420 may be determined based on the rows and columns (e.g., K×P). K and P may be any positive integer (e.g., 1, 2, 3, 6, 8, and 10, etc.). K and P may be the same or different. When the scintillator array 420 is a multi-layer array with K rows, P columns and Q layers, a number of scintillators in the scintillator array 420 may be determined based on the rows, columns and layers (e.g., K×P×Q).

Figure 5B:
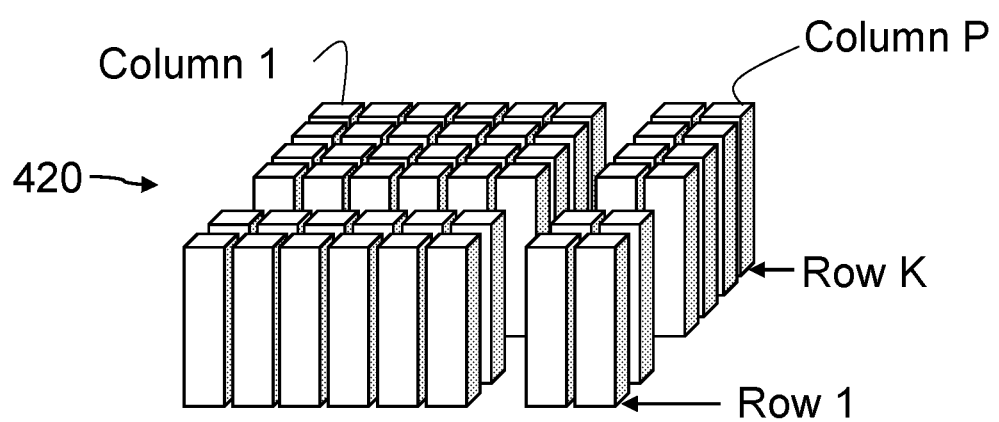
FIG. 5B illustrates a stereogram of an exemplary scintillator array according to some embodiments of the present disclosure.

FIG. 5B illustrates a stereogram of an exemplary scintillator array 420 according to some embodiments of the present disclosure. FIG. 5B uses a single-layer array merely for the purpose of illustration. In some embodiments, the scintillator array 420 may also be a multi-layer array. As shown in FIG. 5B, a number of column of the scintillator array 420 may be P and a number of row of the scintillator array 420 may be K.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, there may be gap spacings between the scintillators in the scintillator array 420. The gap spacings may be filled with a conductive or non-conductive material for shielding the scintillators from external electric field interference.

Figure 6A:
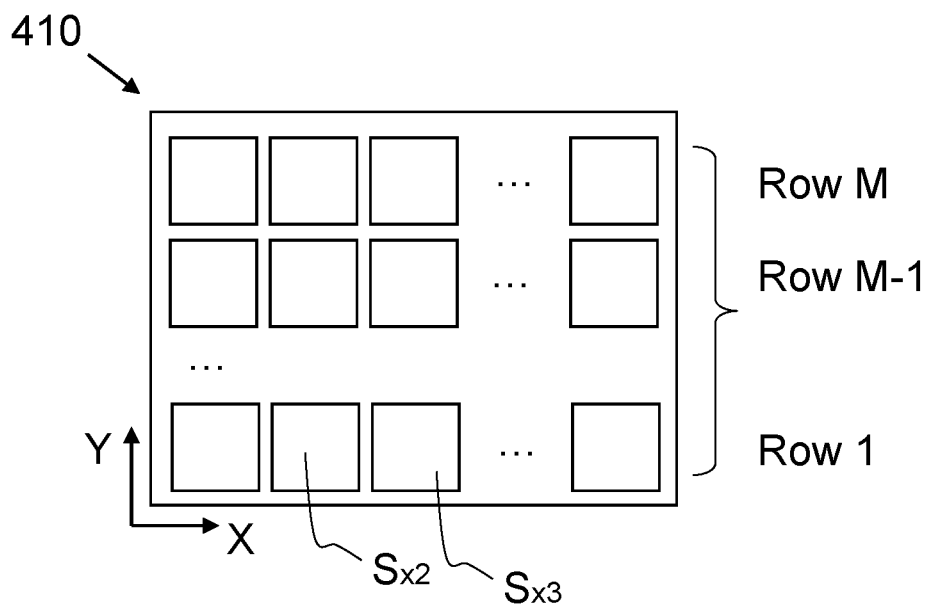
FIG. 6A illustrates a top view of an exemplary first light sensor array according to some embodiments of the present disclosure.

FIG. 6A illustrates a top view of an exemplary first light sensor array 410 according to some embodiments of the present disclosure. The top view is a view of the X-Y plane of the first light sensor array 410. The first light sensor array 410 may be in a layer that is parallel to the X-Y plane. The first light sensor array 410 may include a plurality of light sensors arranged in M rows. The M rows may be parallel to the first direction (e.g., X-axis in the three-dimensional coordinate system). Light sensors in a row (e.g., a light sensor $S_{x2}$ and a light sensor $S_{x3}$ in Row 1) may connect to another light sensor (e.g., an adjacent light sensor) through an electric circuit and share a same electrical signal collection unit (not shown in FIG. 4). For example, the light sensor $S_{x2}$ may connect to the light sensor $S_{x3}$. As another example, the light sensor $S_{x1}$ may connect to the light sensor $S_{x3}$.

Figure 6B:
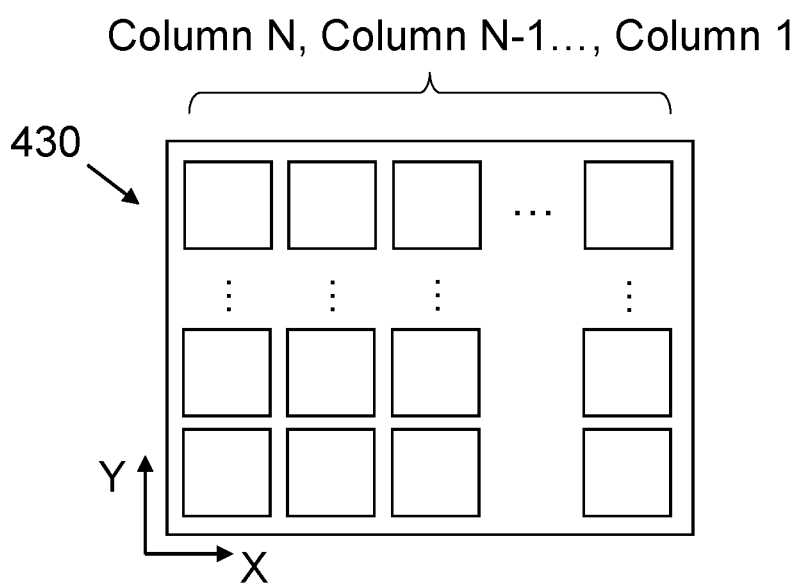
FIG. 6B illustrates a top view of an exemplary second light sensor array according to some embodiments of the present disclosure.

FIG. 6B illustrates a top view of an exemplary second light sensor array 430 according to some embodiments of the present disclosure. The top view is a view of the X-Y plane of the second light sensor array 430. The second light sensor array 430 may be in a layer that is parallel to the X-Y plane. The second light sensor array 430 may include a plurality of light sensors arranged in N columns. The N columns may be parallel to the second direction (e.g., Y-axis in the three-dimensional coordinate system).

In some embodiments, both the number of the plurality of light sensors in the first light sensor array 410 and the number of the plurality of light sensors in the second light sensor array 430 may be less than the number of the scintillators in the scintillator array 420. For example, when the scintillator array 420 includes 16 scintillators, both of the first light sensor array 410 and the second light sensor array 430 may include any number of light sensors that are less than 16 (e.g., 8, 4, etc.). In some embodiments, the number of the plurality of light sensors in the first light sensor array 410 and the number of the plurality of light sensors in the second light sensor array 430 may be the same or different. For example, in a detector unit 310 with a 4×4 scintillator array 420, the first light sensor array 410 and the second light sensor array 420 may include different numbers of light sensors, e.g., four light sensors in the first light sensor array 410 and eight light sensors in the second light sensor array 420. As another example, in a detector unit 310 with a 4×4 scintillator array 420, the first light sensor array 410 and the second light sensor array 420 may include the same numbers of light sensors, e.g., four light sensors in the first light sensor array 410 and four light sensors in the second light sensor array 420, or eight light sensors in the first light sensor array 410 and eight light sensors in the second light sensor array 420.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, gap spacings between light sensors in the first light sensor array 410 may be uniform or non-uniform. For example, a gap spacing between light sensor $Sx_1$ and light sensor $Sx_2$ may be 0.19 nm and a gap spacing between light sensor $Sx_2$ and light sensor $Sx_3$ may be 0.15 nm.

Figure 7A:
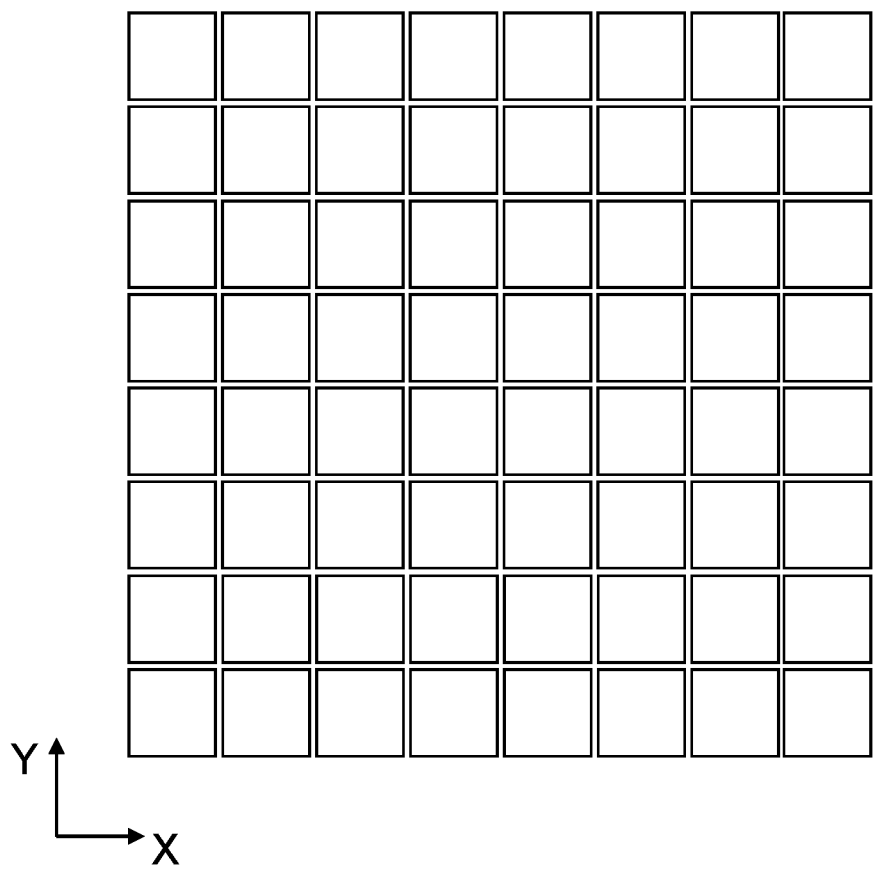
FIG. 7A illustrates a top view of an exemplary 8×8 scintillator array according to some embodiments of the present disclosure.

FIG. 7A illustrates a top view of an exemplary 8×8 scintillator array 710 according to some embodiments of the present disclosure. The top view is a view of the X-Y plane of the 8×8 scintillator array 710. The 8×8 scintillator array 710 may be an embodiment of the scintillator array 420 shown in FIG. 4.

Figure 7B:
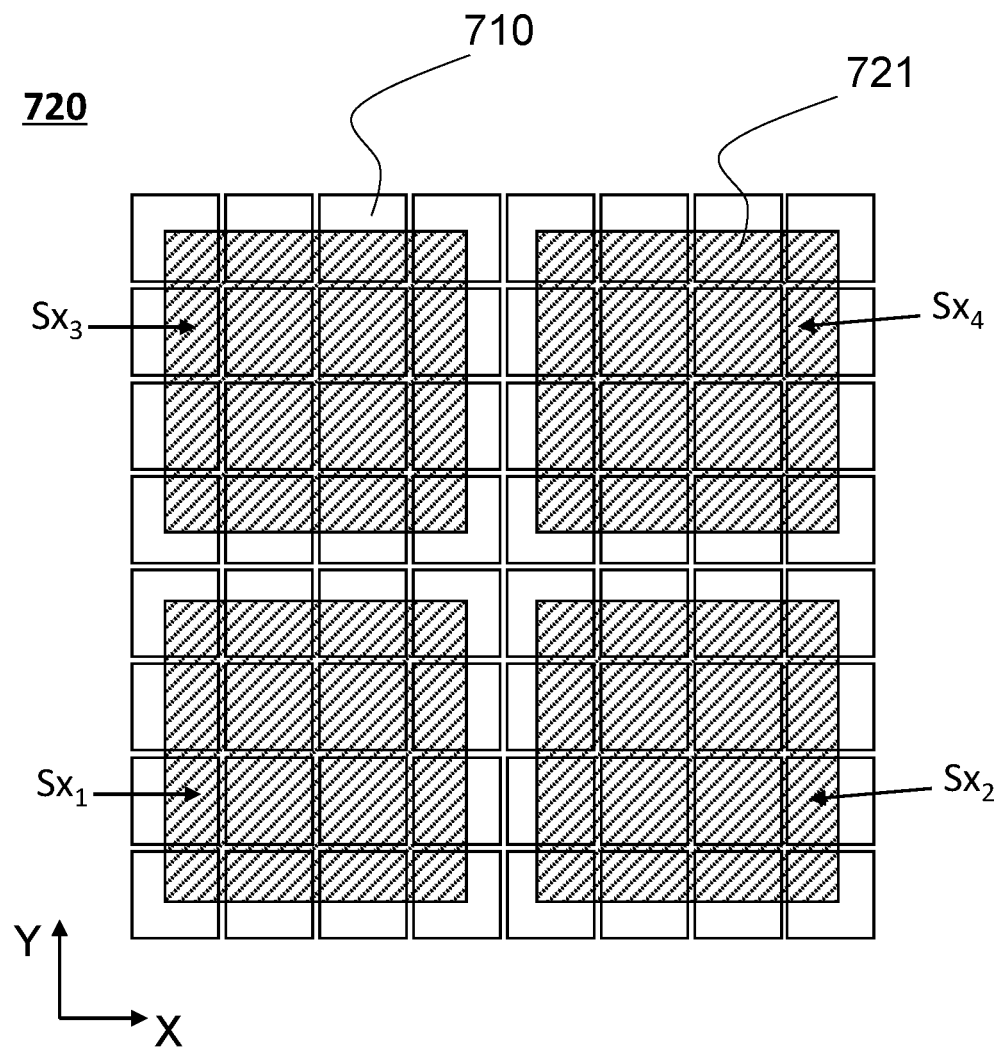
FIG. 7B illustrates a perspective diagram of an exemplary detector unit according to some embodiments of the present disclosure.

FIG. 7B illustrates a perspective diagram of an exemplary detector unit 720 according to some embodiments of the present disclosure. The detector unit 720 may be an embodiment of the detector unit 310 shown in FIG. 4. FIG. 7B shows a perspective diagram of an exemplary detector unit 720 from a top view. The detector unit 720 may include an a first light sensor array 721, the 8×8 scintillator array 710, a second light sensor array (not shown in FIG. 7B). The first light sensor array 721 and the second light sensor array (not shown in FIG. 7B) may have the same number of light sensors (e.g., 4 light sensors). The second light sensor array may not be illustrated as it is beneath the first light sensor array 721 in FIG. 7B.

The first light sensor array 721 may include a light sensor $Sx_1$, a light sensor $Sx_2$, a light sensor $Sx_3$ and a light sensor $Sx_4$. The light sensor $Sx_1$ and the light sensor $Sx_3$ may be in a first row of the first light sensor array 721. The light sensor $Sx_2$ and the light sensor $Sx_4$ may be in a second row of the first light sensor array 721.

The first light sensor array 721 may be configured to acquire a first data set (e.g., $\{X_1, X_2, X_3, \text{and } X_4\}$) based on the light sensors $Sx_1$, $Sx_2$, $Sx_3$ and $Sx_4$. The imaging processing system 100 may determine a light intensity spatial distribution corresponding to an incidence photon in the first direction (e.g., X-axis in the three-dimensional coordinate system).

Figure 7C:
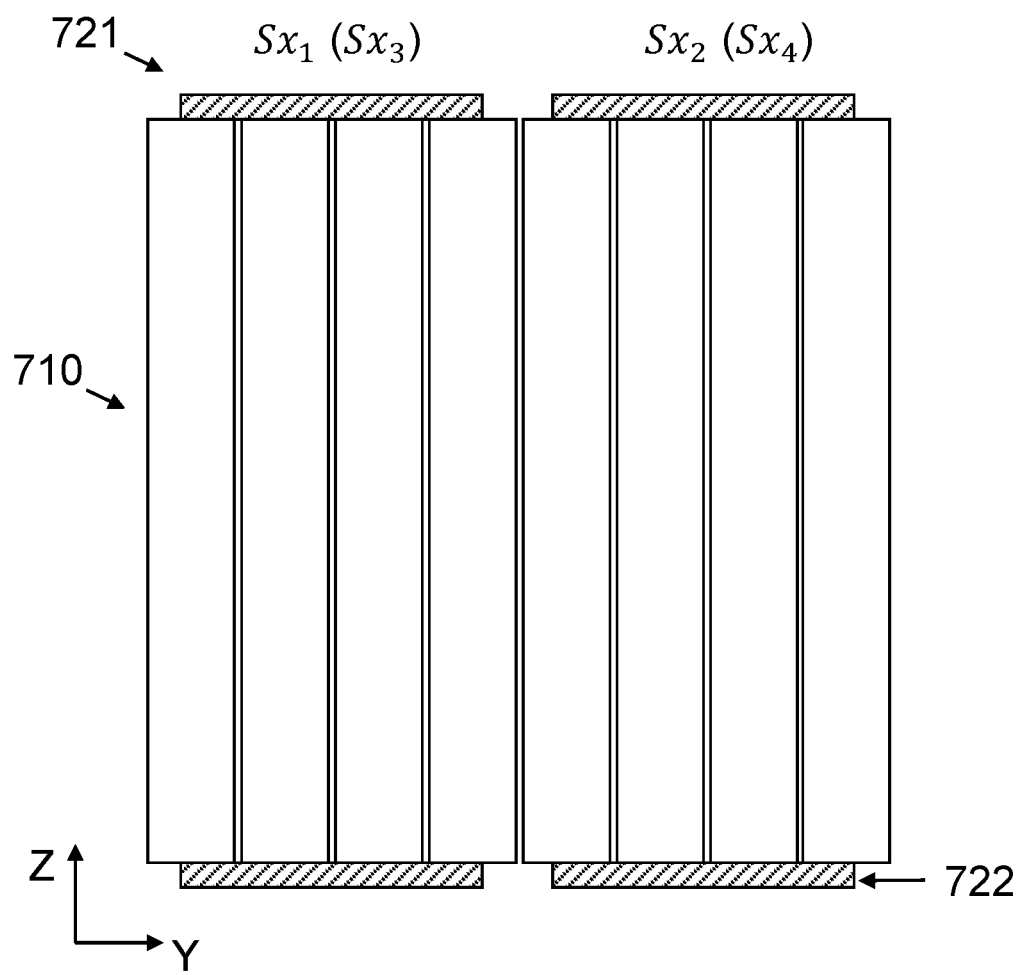
FIG. 7C illustrates a side view of an exemplary detector unit according to some embodiments of the present disclosure.

FIG. 7C illustrates a side view of the exemplary detector unit 720 according to some embodiments of the present disclosure. FIG. 7C may be a side view of the Y-Z plane of the detector unit 720. Only $Sx_1$ of the two light sensors $Sx_1$ and $Sx_3$ in the first row of the first light sensor array 721 may be shown in FIG. 7C. The side view of the Y-Z plane of the detector unit 720 only shows the light sensor $Sx_1$, and the light sensor $Sx_3$ may be behind the light sensor $Sx_1$. Only $Sx_2$ of the two light sensors $Sx_2$ and $Sx_4$ in the second row of the first light sensor array 721 may be shown in FIG. 7C. The light sensor $Sx_4$ may be behind the light sensor $Sx_2$.

Figure 7D:
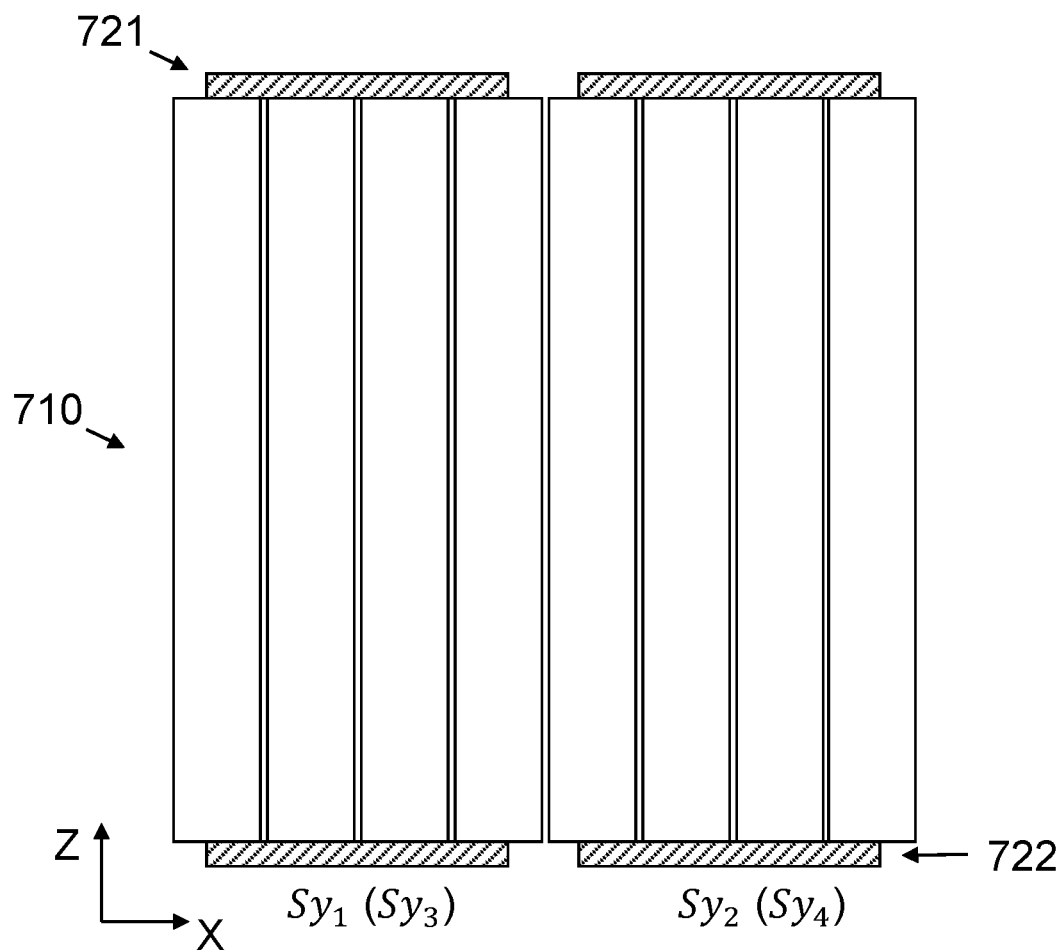
FIG. 7D illustrates a side view of an exemplary detector unit according to some embodiments of the present disclosure.

FIG. 7D illustrates a side view of the exemplary detector unit 720 according to some embodiments of the present disclosure. FIG. 7D may be a view of the X-Z plane of the detector unit 720.

The second light sensor array 722 may include a light sensor $Sy_1$, a light sensor $Sy_2$, a light sensor $Sy_3$ and a light sensor $Sy_4$. The light sensor $Sy_1$ and the light sensor $Sy_3$ may be in a first column of the first light sensor array 722. The light sensor $Sy_2$ and the light sensor $Sy_4$ may be in a second column of the second light sensor array 722. Only $Sy_1$ of the two light sensors $Sy_1$ and $Sy_3$ in the first column of the second light sensor array 722 may be shown in FIG. 7D. The light sensor $Sy_3$ may be behind the light sensor $Sy_1$. Only $Sy_2$ of the two light sensors $Sy_2$ and $Sy_4$ in the second column of the second light sensor array 722 may be shown in FIG. 7D. The light sensor $Sy_4$ may be behind the light sensor $Sy_2$.

The second light sensor array 722 may be configured to acquire a second data set (e.g., $\{Y_1, Y_2, Y_3, \text{and } Y_4\}$) based on the light sensors $Sy_1$, $Sy_2$, $Sy_3$ and $Sy_4$. The imaging processing system 100 may determine a light intensity spatial distribution corresponding to an incidence photon in the second direction (e.g., Y-axis in the three-dimensional coordinate system) based on the second data set.

Figure 8:
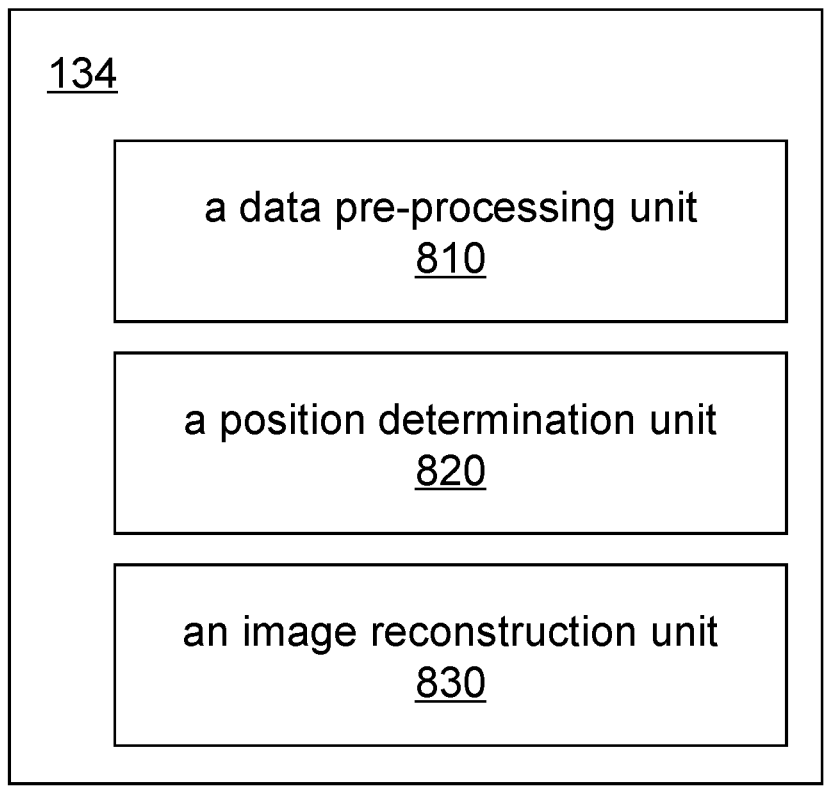
FIG. 8 illustrates a schematic program of an exemplary processing module according to some embodiments of the present disclosure.

FIG. 8 illustrates a schematic program of an exemplary processing module 134 according to some embodiments of the present disclosure. As illustrated in FIG. 8, the processing module 134 may include a data pre-processing unit 810, a position determination unit 820, an image reconstruction unit 830, etc.

The data pre-processing unit 810 may be configured to pre-process a PET data set. The pre-processing the PET data set may include data classification, data screening, data correction (e.g., correction for random coincidences, detector dead-time correction, detector-sensitivity correction), data estimation and subtraction (estimation and subtraction of scattered photons), or the like, or any combination thereof. The pre-processed data set may include multiple sub data sets. In some embodiments, the PET data set and/or the pre-processed data set may be stored in the storage module 133.

The position determination unit 820 may be configured to determine three-dimensional position of an incidence photon corresponding to a target object. The three-dimensional position of the incidence photon may be determined based on the pre-processed data set. The position determination unit 820 may be configured to may determine a position of an annihilation event. The position of an annihilation event may be determined based on the positions of a pair of incidence photons.

The image reconstruction unit 830 may be configured to reconstruct an image of the target object. The image may be reconstructed based on the three-dimensional positions of the incidence photon and the PET data set. The image may be a two-dimensional image or a three-dimensional image. In some embodiments, the image may be displayed on a display of the display module 135.

It should be noted that the descriptions above in relation to the processing module 134 is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, the processing module 134 may include a storage unit (no shown in FIG. 8) to store the pre-processed PET data. Similar modifications should fall within the scope of the present disclosure.

Figure 9:
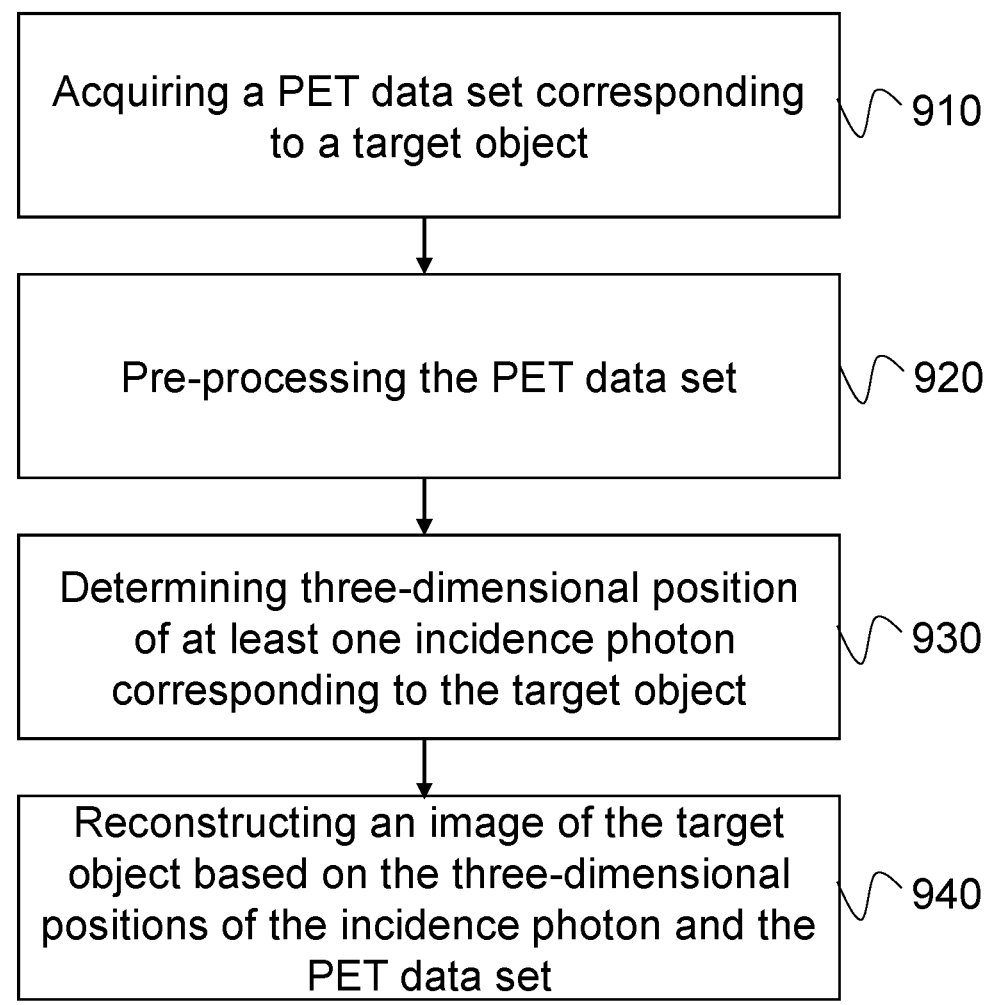
FIG. 9 illustrates a flow chart of a process for reconstructing an image of a target object according to same embodiments of the present disclosure.

FIG. 9 illustrates a flow chart of a process for reconstructing an image of a target object according to same embodiments of the present disclosure. The target object may be a patient that is administered a radiopharmaceutical. The suitability of the radiopharmaceutical may depend, in part, upon the organs or tissues of the target object to be imaged. The radiopharmaceutical may cause an annihilation event (the positron-electron annihilation event 340) that emits a pair of incidence photons (e.g., γ photons) in opposite directions or nearly opposite directions (close to 180°). A pair of detector units (e.g., the detector unit 310 and the detector unit 315) that are placed 180° from each other may detect the pair of incidence photons emitted from a single annihilation event (e.g., the positron-electron annihilation event 340). In some embodiments, a PET system may include more than one pair of detector units and more than one annihilation events. Herein below, a pair of detector units and an annihilation event may be taken as an example in descriptions of the following steps of FIG. 9. The process 900 may be executed by the imaging processing system 100 shown in FIG. 1B. Process 900 may be performed by the imaging processing system 100 shown in FIG. 1B. One or more operations of process 900 may be performed by the computing device 200.

In 910, the imaging processing system 100 may acquire a PET data set corresponding to the target object. In some embodiments, step 910 may be executed by the acquisition module 131 shown in FIG. 1B.

The PET data set may include a plurality of sub data sets acquired by the acquisition module 131 (e.g., a first data set acquired by the detected unit 310, a second data set acquired by the detected unit 315, etc.). The PET data set may include some other data (e.g., information related to the target object) required in an image reconstruction.

In 920, the imaging processing system 100 may pre-process the PET data set. A pre-processed data set may be generated based on the pre-processing operation. In some embodiments, step 920 may be executed by the data pre-processing unit 810 shown in FIG. 8.

The pre-processing of the PET data set may include data classification, data screening, data correction (e.g., correction for random coincidences, detector dead-time correction, detector-sensitivity correction), data estimation and subtraction (estimation and subtraction of scattered photons), or the like, or any combination thereof.

In some embodiments, a first data set and a second data set corresponding to the positron-electron annihilation event 340 of an incidence photon may be determined as a pre-processed data set. The two data sets may be acquired by a pair of detector units (e.g., the detected unit 315 and the detected unit 310) placed 180° from each other in a given time window. For example, the first data set may be $\{X_1, X_2, X_3, \text{and } X_4\}$ described above in connection with FIG. 7C, and the second data set may be $\{Y_1, Y_2, Y_3, \text{and } Y_4\}$ described above in connection with in FIG. 7D.

In 930, the imaging processing system 100 may determine a three-dimensional position of at least one incidence photon corresponding to the target object. In some embodiments, step 930 may be executed by the position determination unit 820 shown in FIG. 8.

The three-dimensional position of the at least one incidence photon may be determined based on the pre-processed data set. In some embodiments, the three-dimensional position of the at least one incidence photon may be determined based on the first data set (e.g., $\{X_1, X_2, X_3, \text{and } X_4\}$) and the second data set (e.g., $\{Y_1, Y_2, Y_3, \text{and } Y_4\}$). Details of determining the three-dimensional position of the at least one incidence photon may be found in FIG. 10, and descriptions thereof.

In 940, the imaging processing system 100 may reconstruct an image of the target object based on the three-dimensional positions of the pair of the incidence photons and the PET data set. In some embodiments, step 930 may be executed by the image reconstruction unit 830.

Based on the three-dimensional positions of the pair of incidence photons, a line of response may be determined between the two positions on the pair of detectors. A position of the annihilation event (e.g., the positron-electron annihilation event 340) may be in the line of response. Such lines of response may be used for reconstruction of an image. The image may be two-dimensional or three-dimensional. For example, based on lines of response corresponding to a single detector ring 320, a two-dimensional image may be reconstructed. A three-dimensional image may be reconstructed based on all of the lines of response detected on the pairs of detector units of multiple detector rings 320. In some embodiments, the position of the annihilation event may be calculated based on the difference between a time of flight (TOF) of the pair of incidence photons and the lines of response.

One or more techniques may be used in the image reconstructing, for example, a filtered back projection (FBP) technique, a statistical, likelihood-based approaches technique, an attenuation correction technique, or the like, or any combination thereof.

It should be noted that process 900 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart from the scope of the present disclosure. For instance, an image combination operation (e.g., combination of PET with CT) may be performed after the image reconstruction. Similar modifications should fall within the scope of the present disclosure.

Figure 10:
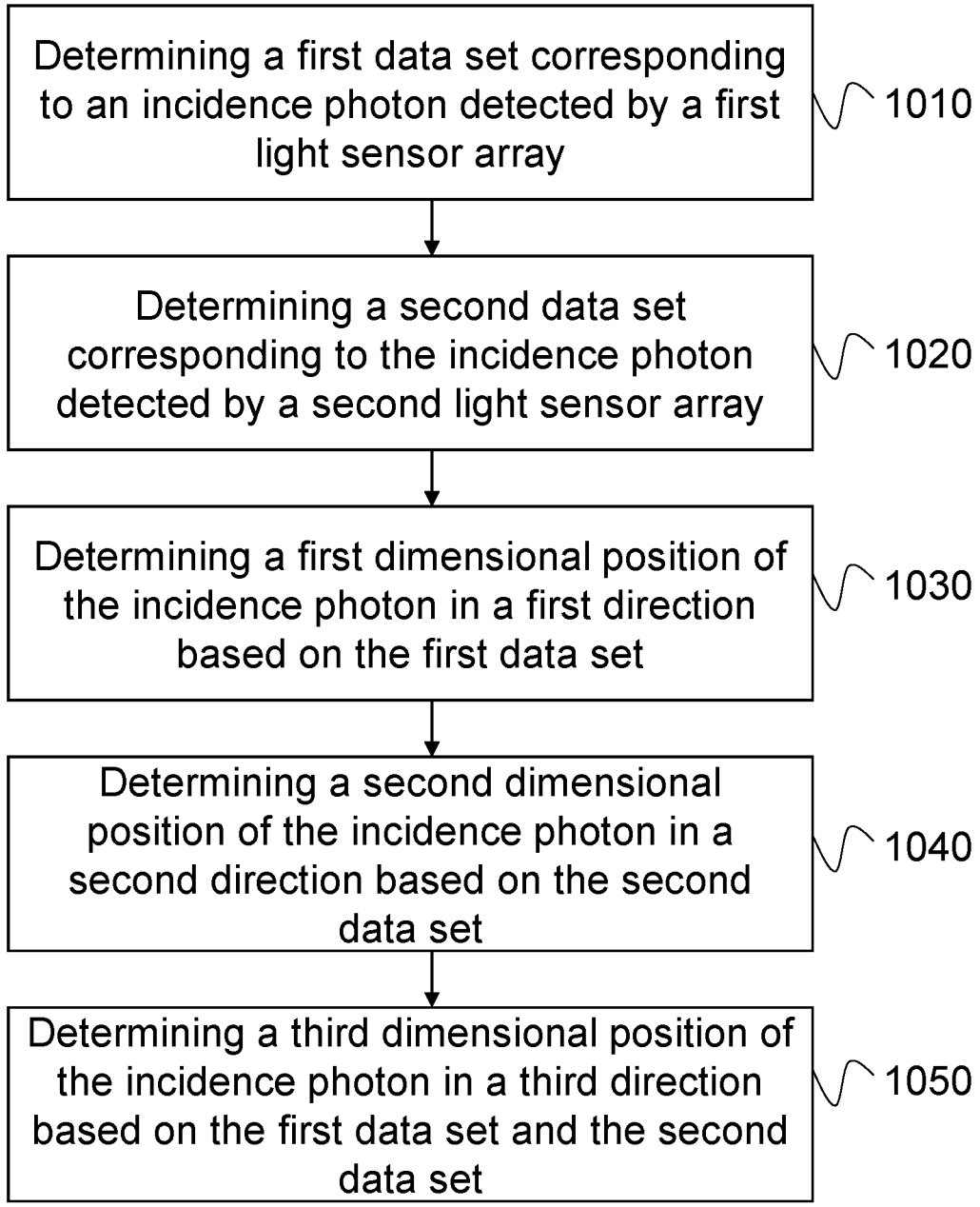
FIG. 10 illustrates a flow chart of a process for determining a three-dimensional position of an incidence photon according to some embodiments of the present disclosure.

FIG. 10 illustrates a flow chart of a process 1000 for determining a three-dimensional position of an incidence photon according to some embodiments of the present disclosure. Process 1000 may be performed by the imaging processing system 100 shown in FIG. 1B. One or more operations of process 1000 may be performed by the computing device 200. In some embodiments, process 1000 described with reference to FIG. 8 may be an exemplary process for achieving 930 shown in FIG. 9.

In 1010, the imaging processing system 100 may determine a first data set corresponding to an incidence photon detected by a first light sensor array.

In some embodiments, the first data set may be data set $\{X_1, X_2, X_3, \text{ and } X_4\}$ as described above in connection with FIG. 7C. The data in the first data set may correspond to a light intensity of a light detected by light sensors of the first light sensor array 721. The light may be generated by the scintillator in the 8×8 scintillator array 710 corresponding to the incidence photon.

In 1020, the imaging processing system 100 may determine a second data set corresponding to the incidence photon detected by a second light sensor array.

In some embodiments, the second data set may be data set $\{Y_1, Y_2, Y_3, \text{ and } Y_4\}$ as described above in connection with FIG. 7D. The data in the second data set may correspond to the light intensity of the light detected by light sensors of a second light sensor array 722. The light may be generated by the scintillator in the 8×8 scintillator array 710 corresponding to the incidence photon.

In 1030, the imaging processing system 100 may determine a first dimensional position of the incidence photon in the first direction based on the first data set. The first dimensional position may refer to a position in the first direction (e.g., X-axis in the three-dimensional coordinate system). The first dimensional position of the incidence photon may be determined based on a first light intensity spatial distribution corresponding to the incidence photon. The first light intensity spatial distribution may be determined based on the first data set.

In some embodiments, the first light intensity spatial distribution may be determined based on data in the first data set. For example, the first data set may be $\{X_1, X_2, X_3, \text{ and } X_4\}$ and the first dimensional position x may be determined by equation (1):

$$x = X_1 + X_3/(X_1 + X_2 + X_3 + X_4). \tag{1}$$

In 1040, the imaging processing system 100 may determine a second dimensional position of the incidence photon in the second direction based on the second data set. The second dimensional position may refer to a position in the second direction (e.g., Y-axis in the three-dimensional coordinate system). The second dimensional position of the incidence photon may be determined based on a second light intensity spatial distribution corresponding to the incidence photon. The second light intensity spatial distribution may be determined based on the second data set.

In some embodiments, the second light intensity spatial distribution may be determined based on data in the second data set. For example, the second data set may be $\{Y_1, Y_2, Y_3, \text{ and } Y_4\}$ and the second dimensional position y may be determined by equation (2):

$$y = Y_1 + Y_3/(Y_1 + Y_2 + Y_3 + Y_4). \tag{2}$$

In 1050, the imaging processing system 100 may determine a third dimensional position of the incidence photon in a third direction based on the first data set and the second data set. The third dimensional position may refer to a position in the third direction (e.g., Z-axis in the three-dimensional coordinate system). The third dimensional position of the incidence photon may be determined based on a third light intensity spatial distribution corresponding to the incidence photon. The third light intensity spatial distribution may be determined based on the first data set and the second data set.

In some embodiments, the third light intensity spatial distribution may be determined based on a coefficient. The coefficient may be a ratio of a sum of the at least first light intensity value in the first data set and a sum of the at least second light intensity value in the second data set. For example, the coefficient $C_z$ may be determined by equation (3):

$$C_z = (X_1 + X_2 + X_3 + X_4)/(X_1 + X_2 + X_3 + X_4 + Y_1 + Y_2 + Y_3 + Y_4). \tag{3}$$

Then the third dimensional position Z may be determined based on $C_z$. For example, Z may be determined by a product of $C_z$ and a thickness of the scintillator in the 8×8 scintillator array 710.

Therefore, the three-dimensional position of the incidence photon in the three-dimensional coordinate system may be determined based on the first dimensional position, the second dimensional position and the third dimensional position of the incidence photon. Based on positions of incidence photons, one or more parameters (e.g., a line of response, a depth of interaction, a position of an annihilation event, etc.) may be determined for image reconstruction.

It should be noted that process 1000 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart from the scope of the present disclosure. For instance, a coordinate conversion operation may be performed after the determination of the three-dimensional position of the incidence photon in order to describe more than one incidence photons in a same coordinate. Similar modifications should fall within the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the operator's computer, partly on the operator's computer, as a stand-alone software package, partly on the operator's computer and partly on a remote computer or entirely on the remote computer or server. In the latter scenario, the remote computer may be connected to the operator's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A Positron Emission Tomography (PET) system, the system comprising:
   at least one processor and a storage;
   an acquisition module configured to acquire a PET data set corresponding to a target object and comprising:
      a scintillator array having a plurality of scintillators arranged in multiple rows and multiple columns;
      a first light sensor array having a first number of light sensors arranged in one or more rows, wherein one light sensor in a row connects through an electric circuit to an adjacent light sensor in the same row and share a same electrical signal collection unit; and
      a second light sensor array having a second number of light sensors arranged in one or more columns, wherein one light sensor in a column connects through an electric circuit to an adjacent light sensor in the same column and share a same electrical signal collection unit, wherein
         a first surface of the scintillator array is optically coupled to the first light sensor array and a second surface of the scintillator array is optically coupled to the second light sensor array,
at least one light sensor of the first light sensor array is optically coupled to at least two rows and at least two columns of scintillators of the scintillator array, and
the first number of light sensors of the first light sensor array or the second number of light sensors of the second light sensor array is less than the number of the plurality of scintillators.

2. The system of claim 1, further comprising
a processing module configured to determine a three-dimensional position of an incidence photon based on the PET data set.

3. The system of claim 1, wherein at least one light sensor in the first light sensor array or the second light sensor array comprises a silicon photomultiplier (SiPM).

4. The system of claim 2, further comprising an image reconstruction unit
configured to reconstruct an image of the target object based on the three-dimensional position of the incidence photon and the PET data set.

5. The system of claim 2, wherein at least one component of the three-dimensional position of the incidence photon in a direction is determined based on a light intensity spatial distribution corresponding to the incidence photon in the direction.

6. The system of claim 1, wherein the PET data set comprises
a first data set comprising at least a first light intensity value corresponding to the incidence photon detected by the first light sensor array, and
a second data set comprising at least a second light intensity value corresponding to the incidence photon detected by the second sensor array.

7. The system of claim 6, wherein
a first dimensional position of the incidence photon in a first direction is determined based on the first data set;
a second dimensional position of the incidence photon in a second direction is determined based on the second data set; and
a third dimensional position of the incidence photon in a third direction is determined based on the first data set and the second data set.

8. The system of claim 6, wherein at least one component of the three-dimensional position of the incidence photon in a direction is related to a coefficient, the coefficient being a ratio of a sum of the at least first light intensity value in the first data set to a sum of the at least second light intensity value in the second data set.

9. The system of claim 1, wherein
the ratio of the first number of light sensors of the first light sensor array to the number of the plurality of scintillators is 2 to 1, and
the ratio of the second number of light sensors of the second light sensor array to the number of the plurality of scintillators is 2 to 1.

10. The system of claim 1, wherein the first number of light sensors of the first light sensor array is equal to the second number of light sensors of the second light sensor array.

11. A method for determining a three-dimensional position of an incidence photon in a Positron Emission Tomography (PET) system, the method implemented on at least one processor and a storage and comprising:
acquiring a PET data set corresponding to a target object; and
determining the three-dimensional position of the incidence photon based on the PET data set, wherein
the PET system comprises a first light sensor array having a first number of light sensors arranged in one or more rows, wherein one light sensor in a row connects through an electric circuit to an adjacent light sensor in the same row and share a same electrical signal collection unit, a second light sensor array, and a scintillator array having a second number of light sensors arranged in one or more columns, wherein one light sensor in a column connects through an electric circuit to an adjacent light sensor in the same column and share a same electrical signal collection unit,
the scintillator array having a plurality of scintillators arranged in multiple rows and multiple columns,
the first light sensor array is optically coupled to a first surface of the scintillator array,
the second light sensor array is optically coupled to a second surface of the scintillator array,
at least one light sensor of the first light sensor array is optically coupled to at least two rows and at least two columns of scintillators of the scintillator array, and
a first number of the light sensors in the first light sensor array is less than a number of scintillator elements in the scintillator array, or a second number of the second light sensor array is less than a number of scintillator elements in the scintillator array.

12. The method of claim 11,
wherein the first number of the light sensors in the first light sensor array is less than the number of scintillator elements in the scintillator array, and the second number of the second light sensor array is less than the number of scintillator elements in the scintillator array.

13. The method of claim 11, wherein at least one light sensor in the first light sensor array or the second light sensor array comprises a silicon photomultiplier (SiPM).

14. The method of claim 11, further comprising
reconstructing an image of the target object based on a three-dimensional position of an incidence photon and the PET data set.

15. The method of claim 14, further comprising:
determining, based on a light intensity spatial distribution corresponding to the incidence photon in a direction, at least one component of the three-dimensional position of the incidence photon in the direction.

16. The method of claim 11, wherein the PET data set comprises
a first data set comprising at least a first light intensity value corresponding to the incidence photon detected by the first light sensor array, and
a second data set comprising at least a second light intensity value corresponding to the incidence photon detected by the second sensor array.

17. The method of claim 16, wherein
a first dimensional position of the incidence photon in a first direction is determined based on the first data set;
a second dimensional position of the incidence photon in a second direction is determined based on the second data set; and
a third dimensional position of the incidence photon in a third direction is determined based on the first data set and the second data set.

18. The method of claim 16, wherein at least one component of the three-dimensional position of the incidence photon in a direction is related to a coefficient, the coefficient being a ratio of a sum of the at least first light intensity value in the first data set to a sum of the at least second light intensity value in the second data set.

19. A non-transitory computer readable medium comprising executable instructions that, when executed by at least one processor, cause the at least one processor to effectuate a method for determining a three-dimensional position of an incidence photon in a Positron Emission Tomography (PET) system, the method comprising:

acquiring a PET data set corresponding to a target object; and determining the three-dimensional position of the incidence photon based on the PET data set, wherein the PET system comprises a first light sensor array having a first number of light sensors arranged in one or more rows, wherein one light sensor in a row connects through an electric circuit to an adjacent light sensor in the same row and share a same electrical signal collection unit, a second light sensor array, and a scintillator array having a second number of light sensors arranged in one or more columns, wherein one light sensor in a column connects through an electric circuit to an adjacent light sensor in the same column and share a same electrical signal collection unit, the scintillator array having a plurality of scintillators arranged in multiple rows and multiple columns, the first light sensor array is optically coupled to a first surface of the scintillator array, the second light sensor array is optically coupled to a second surface of the scintillator array, at least one light sensor of the first light sensor array is optically coupled to at least two rows and at least two columns of scintillators of the scintillator array, and a first number of the light sensors in the first light sensor array is less than a number of scintillator elements in the scintillator array, or a second number of the second light sensor array is less than a number of scintillator elements in the scintillator array.

20. The non-transitory computer readable medium of claim 19, wherein the first number of the light sensors in the first light sensor array is less than the number of scintillator elements in the scintillator array, and the second number of the second light sensor array is less than the number of scintillator elements in the scintillator array.

* * * * *